United States Patent [19]

Riegger et al.

[11] 4,056,454
[45] Nov. 1, 1977

[54] PROCESS FOR THE PREPARATION OF $\alpha,\alpha,\alpha\alpha',\alpha'$-PENTACHLORO-O-XYLENE

[75] Inventors: Paul Riegger, Troisdorf; Hermann Richtzenhain, Much-Scwellenbach; Gunter Zoche, Bonn, all of Germany

[73] Assignee: Dynamit Nobel Aktiengesellschaft, Cologne, Germany

[21] Appl. No.: 710,834

[22] Filed: Aug. 2, 1976

[30] Foreign Application Priority Data

Aug. 9, 1975 Germany .............................. 2535696

[51] Int. Cl.² ............................................... B01J 1/10
[52] U.S. Cl. ............................................... 204/163 R
[58] Field of Search .............. 260/651 R; 204/163 R, 204/163 HE

[56] References Cited

U.S. PATENT DOCUMENTS

| 2,998,459 | 8/1961 | Baker et al. | 260/651 R |
| 3,703,473 | 11/1972 | Lasco | 260/651 R |

OTHER PUBLICATIONS

Harvey et al., J. Applied Chem. (London) 4, June 1954.

Primary Examiner—Leland A. Sebastian
Attorney, Agent, or Firm—Burgess, Dinklage & Sprung

[57] ABSTRACT

Process for the preparation of $\alpha, \alpha,\alpha,\alpha',\alpha'$-pentachloro-o-xylene by the reaction of o-xylene with chlorine in the presence of solvent and under actinic light radiation, characterized in that the reaction is performed at temperatures above 75° up to 140° C with carbon tetrachloride as solvent, with the introduction of chlorine, or in some cases by means of chlorine activated in the gas phase.

7 Claims, 1 Drawing Figure

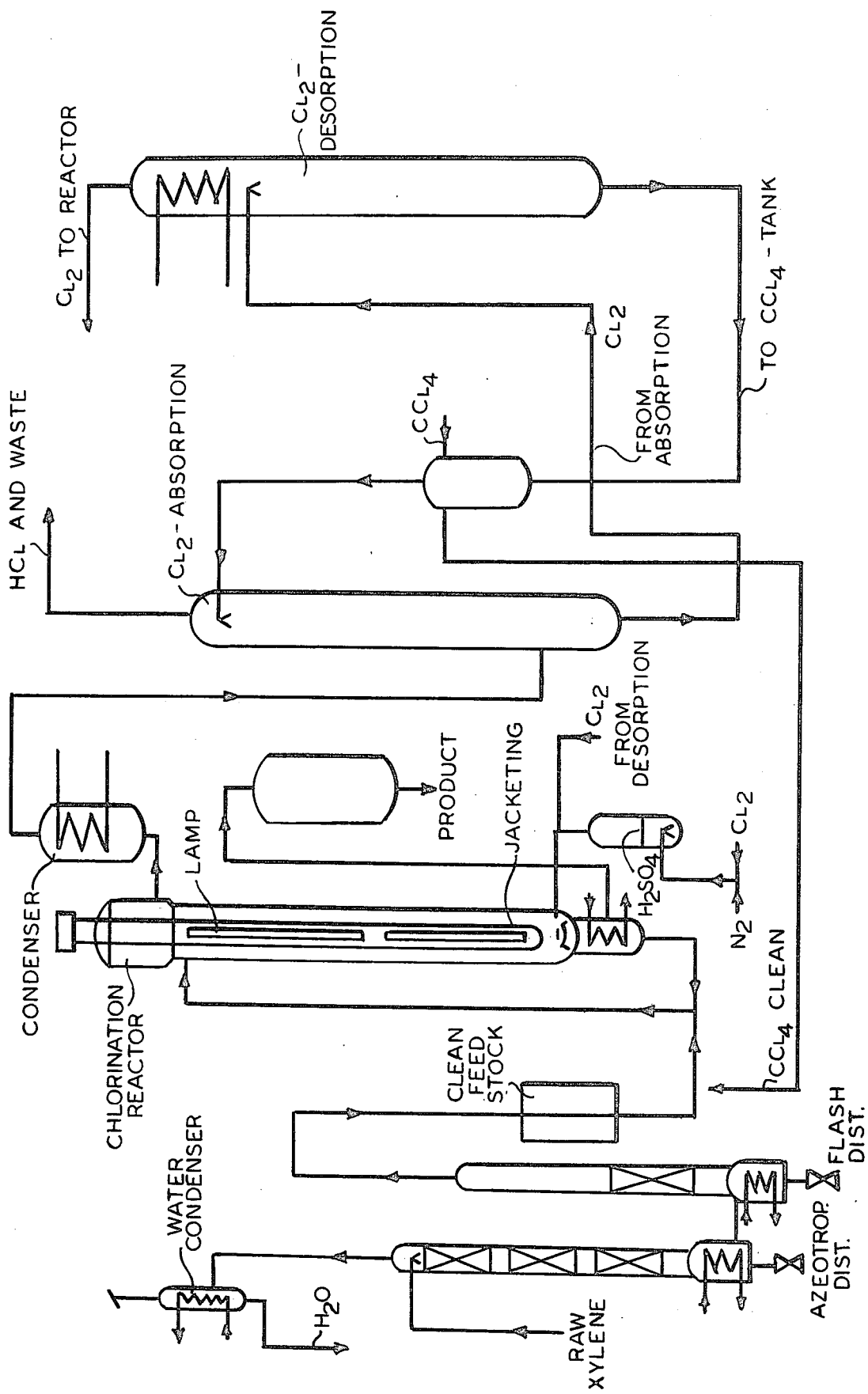

PROCESS FOR THE PREPARATION OF α,α,αα',α'-PENTACHLORO-O-XYLENE

BACKGROUND

The present invention relates to a process for the preparation of α, α, α, α', α'-pentachloro-o-xylene by the photochlorination of o-xylene.

In o-xylene, only 5 of the 6 hydrogens of the side chain can be replaced by Cl. The literature on the preparation of o-pentachloroxylene is not very plentiful, and is mostly contained in the literature on the chlorination of m-xylene and p-xylene. The methods of preparation are the same as the method of radical chlorination. Colson and Gouthier (A.Ch. (6) 11, 26) chlorinated with $PCl_5$. Light, or radical forming catalysts are used as radical sources (A. E. Kretow et al., Z. Abscei Chimii 30, 3019–24 (1960), German Reich Patent 668,033, DL Patent 9,096, E. T. McBee et al. Natl. Nuclear Energy Ser. Div. VII, 1,207–21 (1951), Harvey et al, J. Appl. Chem., 4, 319–25 (1954). Data concerning yield and purity are lacking in most of the literature. According to McBee et al., a product forms in the chlorination of o-xylene which contains 67.1% chlorine, but the theoretical chlorine content of o-pentachloroxylene is 63.7%. Only by distillation is a product considered as pure obtained with 64.1% chlorine plus higher-boiling fractions containing 67.5 and 78.2% chlorine. But distillation residues, which certainly are produced, are not mentioned, but decompositions towards the end of the distillation are mentioned.

Excessively high chlorine contents are to be attributed to chlorination in the nucleus and chlorolysis. Chlorolysis leads primarily to products of low chlorine content. A. E. Kretow finds, in addition to the main product, an oil having a lower chlorine content of 51%.

Since in the chlorination of o-xylene one must expect unexplained secondary reactions in addition to the known reactions, the preparation of a pure product is difficult.

THE INVENTION

It is the object of the invention to arrive, through a combination of measures for the suppression of secondary reactions, at a product of higher technical purity which can be used without further refinement operations for the production of secondary products.

The following secondary reactions are known only partially and in general outline from the literature and have been recognized as the cause of by-products which occur:

1. Reactions which are promoted by Friedel-Crafts catalysts; they include:
   a. Chlorination in the nucleus, the speed of the nuclear chlorination being increased by the presence of the said catalysts, especially by the omnipresent iron compounds. Traces of moisture also catalyze nuclear chlorination by the formation of halogen cations. The tendency towards nuclear chlorination is considerably diminished with each substituted chlorine in the side chain, so that nuclear chlorination is especially acute in the initial phase of the chlorination.
   b. Friedel-Crafts alkylation, also catalyzed especially by iron impurities, likewise has its greatest probability in the initial phase of the chlorination, especially through the formation of condensation products of methylbenzylchloride and xylene with the yielding of HCl, these products being subsequently chlorinated.
   c. Another secondary effect of traces of metals, especially iron, is the formation of colored complex compounds whose inherent light absorption interferes with the photoreaction.

2. Photodimers are unavoidable, especially at the beginning of the chlorination, since the irradiation of the reaction mixture with very powerful light sources and accordingly high quantum densities produces not only chlorine radicals as initiators for the side-chain chlorination, but also xylene radicals in relatively high concentration, which dimerize to dimethyldiphenylethane derivatives and likewise become chlorinated.

3. Chlorolysis takes place in the final phase of the chlorination, especially as a consequence of the ortho-substitution. Under the influence of chlorine, the pentachloro-o-xylene splits off tri- and dichloromethyl groups, and o-chlorobenzalchloride, o-chlorobenzotrichloride, carbon tetrachloride and chloroform are formed, among other substances. o-Chlorobenzalchloride becomes partially further chlorinated and chloroform virtually entirely further chlorinated to o-chlorobenzotrichloride and carbon tetrachloride. While in the case of derivatives of m- and p-xylene this reaction takes place only at very high temperatures, the chlorolysis of chlorinated o-xylenes takes place as soon as the temperature rises above 100° C. On the one hand, an economical rate of chlorination requires higher temperatures towards the end of the chlorination, and on the other hand, the chlorolysis also increases as the temperature rises. The chlorolysis is dependent upon time and temperature, i.e., the timely stopping of the reaction is essential. A compromise must be made between the content of chlorolysis products and tetrachloro-o-xylene, depending on purity requirements.

The subject matter of the invention is a process for the preparation of α, α, α, α', α'-pentachloro-o-xylene by the reaction of o-xylene with chlorine in the presence of solvents and under actinic light radiation, which is characterized in that the reaction is performed at temperatures above 75° up to 140° C with carbon tetrachloride as solvent with the introduction of chlorine or in some cases by means of chlorine activated in the gas phase i.e. in the reactor above the reaction mixture.

Temperatures are advantageously used in the reaction which increase from about 80° C at the beginning to about 130° C at the end of the reaction.

The process thus identified succeeds in overcoming the above-mentioned difficulties and in producing, in a single-step process, a pure pentachloro-o-xylene chlorinated only in the side chain (o-PCX).

The nearly complete freedom from compounds chlorinated in the nucleus and the almost complete absence of of condensed compounds which cannot be distilled or distilled only at high temperatures is achieved only by the combination of the above-named process features, additional improvements being achievable by additional advantageous measures which are yet to be specified herein.

The secondary reactions can be minimized by the avoidance of Friedel-Crafts catalysts on the one hand and the intensification of the irradiation on the other, combined with a high rate of throughput.

In this manner an o-PCX is therefore produced which, due to the method whereby it is made, is high in purity and colorless, so that refining operations such as distillation or recrystallization can be dispensed with.

A product prepared in this manner will comply, for example, with the requirements for its further processing to form, for example, o-phthalic aldehyde acid.

A number of the measures adopted in this process were accessible in the state of the art, either from processes for the preparation of p- and m-hexachloroxylenes or from processes for the chlorination of other hydrocarbons, these known processes being able to comprise innumerable alternative features which are not used in the present process, so that the value of the present process is to be seen in the novel selection and, in some cases, combination of measures.

The temperatures of the process are generally between 75° and 140° C, preferably between 80° and 130° C. The reaction is normally conducted at normal pressure or at the pressure resulting from the self-pressure of the reactants on the one hand and the counterpressure of the apparatus. A slight overpressure of 2 atmospheres is acceptable.

In a preferred embodiment, the chlorination is started at low temperatures ranging from about 75° to 85° C and the temperature is increased, first to about 120° C and then to 130° C towards the end of the reaction, and as the reaction progresses the amount of carbon tetrachloride is reduced by distilling it off.

In the first phase of the reaction at low temperature, the light source is operated first at reduced power and chlorine is fed in at such a rate that either no chlorine at all or only negligible amounts of it are contained in the exhaust gas. The reaction heat is therefore carried off substantially as the evaporation heat of the solvent.

In the second phase, after about 3 to 5 hours of reaction time, the output of the light source is increased to full power, chlorine now appearing in the vapor chamber.

It is desirable to absorb this chlorine in an absorption column with a counter-current of carbon tetrachloride and thus to separate it from the hydrogen chloride gas that is formed. In a desorption column connected to the output of the absorption column and operated under pressure, this chlorine can be removed from the solution and recycled to the reactor.

The absorption column likewise serves for the liquefaction of the evaporated carbon tetrachloride and for the condensation of vapors of the starting substances and their low chlorination products.

It is very desirable and advantageous prior to the reaction to refine by distillation the o-xylene and the carbon tetrachloride used as the solvent, and also any auxiliary substances that may be used. This, of course, will remove therefrom any impurities which are introduced into them by the process used in making them and are presumed to be mostly absent, and which are removable by distillation, but in particular it will remove relatively small residues of water and traces of metal or metal salts, and oxygen of the air which may be dissolved in them, and also substances which might find their way into the starting substances and the solvent during the storage and transport thereof.

In the case of the o-xylene, an azeotropic distillation is generally first performed, the water being removed continuously by a water separator at the top of the column. If the solubility of the water is around 0.02 g per 100 ml at 25° C, it is generally desirable, and also sufficient, to reduce it to 0.004 to 0.001 g per 100 ml. The sump product of this column is then subjected to a flash distillation in which rapid heating produces a rapid transfer of the products to be distilled. Traces of metals and metal salts, especially of iron, remain in the concentrate in this flash distillation column. The minimum requirement in this case is that the iron content be reduced below one part per million. A flash distillation generally achieves iron contents of 0.001 ppm and less.

In the replacement of carbon tetrachloride losses, first a flash distillation is performed for the removal of the iron, and in the process an azeotropic distillation is performed to remove moisture. (see example 3).

It is furthermore desirable that the starting substances and solvents thus refined be used either directly or stored in inert reservoirs so as to avoid the danger of recontamination.

For the same reason it is desirable that all of the apparatus used in the process of preparation be made of glass and of enameled materials, and be equipped with inert valves, fittings and measuring apparatus. It is desirable to make such apparatus parts of inert materials such as glass or fluorinated polymers, especially polytetrafluorethylene, or to coat them with such polymers. Suitable fluoropolymers are, for example, the polymerization products of fluorinated, especially perfluorinated, ethylene and propylene, vinyl fluoride and vinylidene fluoride, or copolymers of vinylidene fluoride and tetrafluorethylene, etc.

Materials other than those named above are also usable, such as sufficiently inattackable metals such as tantalum, and under certain conditions nickel, but they must not yield to the reactants any traces of metal acting catalytically in the manner described above, or even light-absorbing metal compounds. For the same reason, the apparatus will remain unopened insofar as possible, since moisture and air as well as minute amounts of dust will greatly contaminate the product if not render it unusable.

By taking the measures described above it will be very advantageously possible to operate in the absence of additives, especially those which bind or mask by complexing traces of metal but in turn may give rise to undesirable reactions or may themselves constitute contaminants of the products in view of the desired high purity of the latter.

The chlorine that is used, which is usually stored in iron containers, is washed conventionally with concentrated sulfuric acid before the reaction, or is purified with conventional absorbing agents and dried, in order again to exclude metal traces and moisture.

The reaction is performed under the action of actinic light from a high-pressure mercury immersion lamp emitting radiation both in the visible and in the ultraviolet wavelengths. It has been found surprisingly that, for an optimum performance of the reaction, there is a maximum limit for the amount of light, which it is best not to exceed. As maximum limit of the light is regarded a light which effects a undistillable residue of the product of not more than 1.0%.

As already described, the output of the light source is reduced in certain phases of the reaction. For practical purpose the minimal working amount of light is tested out, just to prevent in sure manner a maximum of light, by minimizing the number of lamps, the reduction of the burner output of the lamps or by filling in a more absorptive liquid in the jacket of the lamp, as long as the conversion rate is not lowered.

Furthermore, it has proven desirable to provide the high-pressure mercury immersion lamp with a jacket, such as a glass bulb, for example, which is filled with an organic liquid, for example, absorbing parts of the radiation. The use of a suitable liquid in the jacket will not only very appreciably reduce the discoloration of the reaction product, but also prevent the formation of a coating on the lamp. The thickness of the layer of partially absorbing liquid in the jacket can amount to approximately 5 to approximately 70 millimeters. The jacketing not only increases the radius of emergence of the light stream and therefore reduces the quantum density thereof, but also reduces harmful radiation by absorption. Furthermore, the liquid jacket carries away lamp heat, so that the lamp is protected against overheating. Suitable liquids for filling this jacket have been found to be higher aliphatic alcohols, glycols or paraffin oil, or mixtures thereof. Water is unsuitable on account of its lower boiling point. It is desirable to test such liquids for their performance under irradiation, and to select those whose absorption does not increase greatly at 350 to 430 millimicrons. Absorptivity depends on traces of impurities, and is checked at monthly intervals during operation, the liquid being changed if necessary.

The solvent carbon tetrachloride can best be recirculated, the amount of circulating carbon tetrachloride being reduced as the degree of chlorination advances, the amount present at the beginning of the chlorination being 5 to 30% by weight, preferably 5 to 20% by weight, with respect to the o-xylene put in.

The recirculation of the liquid carbon tetrachloride and its evaporation provides a means for the control of the temperature of the reaction, especially in the initial, highly exothermic period of the chlorination.

Towards the final period, supplementary heating is generally provided.

Furthermore, the above-described absorption and desorption of the unreacted chlorine and the recycling thereof is made possible by the recirculation of the carbon tetrachloride.

It is furthermore preferred to shield the apparatus with inert gases, such as nitrogen especially, in order to prevent the entry of oxygen or moisture. For the same purpose the apparatus is also rinsed with inert gas before the reaction.

The process of the invention for the chlorination of o-xylene yields the o-pentachloroxylene in a virtually quantitative manner.

It is furthermore remarkable that, in contrast to numerous known processes, a virtually complete chlorine utilization is achieved, resulting not only in good economy, but also low contamination of the environment by sewage or exhaust gas.

BRIEF DESCRIPTION OF THE DRAWING

The Drawing illustrates the reactor used to carry out the reaction and contains a chlorination reactor and means to recycle the reactants and products.

EXAMPLES

The information given in the examples is intended to further explain details of the process as well as desirable and advantageous embodiments thereof, but it contains no limitation of the invention.

EXAMPLE 1

The chlorination is performed in a cylindrical reactor of glass having a height of 3.75 m and an inside diameter of 450 mm.

In the reactor is suspended a tubular immersion lamp of 50 mm diameter containing two high-pressure mercury radiators mounted one above the other, each of a one meter burner length (TQ 2024, Original Hanau, 2 kW, controllable burner output). The immersion lamp is surrounded by a jacketing tube of 150 mm diameter made of Duran or Pyrex glass. The jacket chamber is filled with paraffin oil (thickness of oil layer 47 mm).

At the upper end of the reactor is an outlet connected to reflux condensers for evaporated solvent.

At the bottom end there is an outlet for draining and for a forced circulation system with pump. In the circuit there is a heat exchanger serving to heat the charge, to add heat towards the end of the chlorination, and to cool down the contents of the reactor before they are drained.

Glass frits at the bottom of the reactor serve for the introduction of chlorine.

All parts of the reactor consist of glass or Teflon.

The reactor is charged with 235 kg (269 liters at about 25° C) of o-xylene with a purity of 99.8% and 45 kg of carbon tetrachloride, after they have been treated as in Example 3 for the removal of traces of iron, moisture and oxygen gas. After this mixture has been heated at 80° C and the lamps have been turned on, initially at reduced output, i.e. with only one lamp reduced from 2.0 to 1.2 kw. chlorine is introduced at a throughput of 90 kg/h which is nearly the maximum achievable rate velocity. A turbulent column of bubbles forms in the reactor, and a strong reflux occurs in the condensers. The exhaust gas passes through the absorption column and goes from there to the hydrochloric acid absorption. The chlorine feed rate is sustained for 4 hours until chlorine emerges. During this period of 4 hours the power of the lamps is increased stepwise to full output.

80 kilograms per hour of the carbon tetrachloride continually being distilled out from the reactor and are substituted by condensed are recycled carbon tetrachloride.

The temperature increases to 130° C.

The absorption column is then used in order to absorb chlorine, and the sump product which previously was being recycled to the reactor now goes to the desorption. The desorbed chlorine returns to the reactor. The chlorine throughput is diminished to such an extent that the continuously measured transformation, measured by formed HCl is maintained at about 80%. The temperature is maintained at 130° C, ultimately by an input of heat, as needed, through the heat exchanger in the reactor circulating system. During this period no new carbon tetrachloride is added and about 95% of the dissolved carbon tetrachloride is driven off. After the chlorine absorption has ended, the residual chlorine and hydrogen chloride are purged with nitrogen. The chlorination time amounts to about 15 hours. The batch is cooled to 80° – 90° C and bottled.

Two specimens are taken for a determination of purity. The one specimen is used for testing by gas chromatography including the volatile by-products. In the other specimens the non-distillable condensed products are determined by vacuum distillation at 10 Torr.

The yield of o-PCX amounts to 618 kg, i.e., virtually 100%. The gas chromatographic purity is 98.5%, with 0.2% o-chlorobenzal chloride, 0.8% o-chlorobenzotrichloride and 0.5% sym.-tetrachloro-o-xylene; the non-distillable residue is 0.2%; in other words, the yield of pure $\alpha, \alpha, \alpha, \alpha', \alpha'$-pentachloro-o-xylene amounts to 98.3% with respect to the pure o-xylene input (M.P. 109°–112° C). The product is only slightly yellowish and does not alter in storage.

EXAMPLE 2

In the same apparatus, under otherwise identical conditions, the following experiments were performed.

The chlorination time was (a) made less than that of Example 1, in which case the chlorolysis products content increases and the content of incompletely chlorinated tetrachloro-o-xylene decreases, and (b) increased above that of Example 1, in which case the content of chlorolysis products decreases and that of tetrachloro-o-xylene increases.

Product Composition

| | o-Chloro-Benzal chloride | o-Chloro-Benzotri-chloride | Chloroxylene Tetra | Chloroxylene Penta |
|---|---|---|---|---|
| a) | 0.31 | 1.66 | 0.01 | 97.55 |
| b) | 0.23 | 0.38 | 1.57 | 97.70 |
| | The end temperature was 140° C | | | |
| c) | 0.33 | 1.1 | 0.5 | 97.6 |

EXAMPLE 3

Purification of xylene and carbon tetrachloride by azeotropic dehydration.

The raw xylene as delivered is pumped into a settling tank where any water droplets present settle on the bottom and are drained out. It is pumped from this tank through a rotameter continuously at a rate of about 15 to 20 liters per hour to a column. The column consists of glass and has three one-meter sections of 100 mm diameter with a Raschig ring packing. At the bottom is a circulating evaporator with an overflow, the output of which is adjusted so as to assure a small reflux to the column. At the top of the column is a reflux condenser with a water separator. The xylene phase is recycled to the column; the small amounts of water run out, and at the same time dissolved air is driven off.

In the state of equilibrium azeotropically dehydrated xylene collects at the bottom of the column, and has on the average only one-tenth of the water content with respect to the equilibrium solubility of water at 20° C.

From the overflow at the bottom a second evaporator is supplied, in which the xylene is totally distilled in a flash distillation column and passes through a condenser into a collecting tank from which the reactor charges are taken. Both the tanks and the stills are under a nitrogen atmosphere.

Carbon tetrachloride, which on the basis of its vapor pressure escapes with the hydrogen chloride, is separated in the HCl absorption system in a phase separator, and is separated from the aqueous hydrochloric acid and dehydrated in a 3-meter column (nominal diameter 100 cm, packed with Raschig rings) as in the case of the xylene distillation described above, and pumped into a pressure reservoir of enameled metal. Carbon tetrachloride losses are made up by feeding raw carbon tetrachloride through a short-path still into the carbon tetrachloride dewatering column.

The distillations take place at normal pressure at the known boiling points.

In the following table, L represents the equilibrium solubility of water at 25° C, B.P. 760 the boiling point in degrees Celsius, Az the boiling point in ° C of the aqueous azeotrope, and G the content of xylene and carbon tetrachloride in the aqueous azeotrope, in weight-percent.

| | L | B.P. 760 | Az | G |
|---|---|---|---|---|
| o-xylene | 0.0175 | 144.41 | 93.5 | 50.1 |
| carbon tet | 0.01 | 76.75 | 66.0 | 95.9 |

EXAMPLE 4

The chlorination is performed in a tubular reactor of Duran glass about 2 m high and 200 mm in diameter, which is provided with a positive circulation, a chlorine inlet at the bottom, and two superimposed condensers. The light source is constituted by 6 externally disposed 250 watt high-pressure mercury lamps (Type HRLS of Radium Elektrizitats-GmbH). The reactor, which is freed of oxygen by purging with nitrogen gas, is filled with about 43 kg of o-xylene and about 15 kg of carbon tetrachloride. Both the o-xylene and the carbon tetrachloride have been rendered free of water and free of traces of metal, especially iron, by preliminary treatment by distillation. The apparatus itself contains no metal parts, consisting only of glass and Teflon fittings. In the circulation system is a heat exchanger which can be used for either heating or cooling. At approximately 80° C, with three lamps operating, chlorination is performed with a chlorine throughput of approximately 5 to 6 kg/h. The chlorine (and the nitrogen as well) is purified in a washer with sulfuric acid and dried. The temperature rises over a period of 2 h to about 125° C and is controlled by the addition of carbon tetrachloride and oil cooling in the positive circulation system such that it reaches 130° C after about 10 h. Two hours later all six lamps are put into operation simultaneously. After ten hours the chlorine transformation still amounts to only 80%, and drops still further at the end about 14 hours later. After purging with nitrogen gas and cooling to 80° C, the contents of the reactor are bottled. The o-xylene put in had a purity of 98.5%, with substantially 1.5% of low-boiling aliphatic hydrocarbons as impurities.

The gas chromatographic analysis of the end product showed a purity of 97.8%, with 0.24% o-chlorobenzal chloride, 0.45% o-chlorobenzotrichloride, 1.30% sym. tetrachloro-o-xylene, and 0.2% o-xylene derivatives chlorinated in the nucleus.

The undistillable content amounted to 3.3%.

What is claimed is:

1. Process for the preparation of $\alpha,\alpha,\alpha,\alpha',\alpha'$-pentachloro-o-xylene consisting essentially of reacting o-xylene with chlorine in the presence of carbon tetrachloride as solvent under actinic light radiation, at temperatures above 75° up to 140° C, the temperature being increased from about above 75° – 90° C at the beginning to about 110 – 140 at the end of the reaction, carbon tetrachloride vapor being evolved during the reaction and the vapor being condensed and recirculated to the reaction, the actinic light radiation source being a high-pressure mercury immersion lamp which is surrounded by a jacket filled with organic liquid which partially absorbs the radiation, the reaction being carried out in the absence of additive which binds traces of metal.

2. Process of claim 1, characterized in that the amount of carbon tetrachloride is 5–35 wt.-% with respect to the xylene put in.

3. Process of claim 1, characterized in that chlorine is evolved during the reaction and evolved chlorine is recycled into the reaction.

4. Process of claim 3, characterized in that evolved chlorine is absorbed in carbon tetrachloride and, after desorption from the latter, is recycled into the reaction.

5. Process of claim 1, characterized in that the reaction is performed in apparatus of at least one of glass, enameled metal, fluorinated polymers, and the metals tantalum and nickel.

6. Process of claim 1, wherein the iron content of the o-xylene is below 1 ppm.

7. Process of claim 1, wherein the yield of the pentachloro-o-xylene is 98.3%.

* * * * *

UNITED STATES PATENT AND TRADEMARK OFFICE
CERTIFICATE OF CORRECTION

PATENT NO. : 4,056,454
DATED : November 1, 1977
INVENTOR(S) : Paul Riegger, Hermann Richtzenhain and Gunter Zoche It is certified that error appears in the above-identified patent and that said Letters Patent are hereby corrected as shown below:

Column 7, line 12, change "less" to --longer--.

Column 7, line 15, change "increased" to --decreased--.

Signed and Sealed this

Thirty-first Day of October 1978

[SEAL]

Attest:

RUTH C. MASON
Attesting Officer

DONALD W. BANNER
Commissioner of Patents and Trademarks